(12) United States Patent
Coon et al.

(10) Patent No.: US 7,338,497 B2
(45) Date of Patent: Mar. 4, 2008

(54) FEMORAL IMPACTOR-EXTRACTOR

(75) Inventors: Thoms M. Coon, Redding, CA (US); Alfred J. Tria, Jr., Princeton, NJ (US); Donald M. Smucker, Perrysburg, OH (US)

(73) Assignee: MIS-TKA Group, LLC, Perrysburg, OH (US)

( * ) Notice: Subject to any disclaimer, the term of this patent is extended or adjusted under 35 U.S.C. 154(b) by 434 days.

(21) Appl. No.: 10/730,841

(22) Filed: Dec. 5, 2003

(65) Prior Publication Data

US 2005/0124998 A1   Jun. 9, 2005

(51) Int. Cl.
*A61F 2/00* (2006.01)

(52) U.S. Cl. ...................................... 606/99

(58) Field of Classification Search ............. 623/13.16, 623/13.12, 23.23, 20.14; 606/86–88, 90, 606/99
See application file for complete search history.

(56) References Cited

U.S. PATENT DOCUMENTS

| | | | | |
|---|---|---|---|---|
| 2,362,957 A | * | 11/1944 | Hackett | 606/86 |
| 2,970,592 A | * | 2/1961 | David | 606/238 |
| 4,004,581 A | * | 1/1977 | Heimke et al. | 606/82 |
| 4,100,626 A | * | 7/1978 | White | 623/21.12 |
| 4,501,266 A | * | 2/1985 | McDaniel | 606/90 |
| 5,002,547 A | * | 3/1991 | Poggie et al. | 606/88 |
| 5,059,196 A | * | 10/1991 | Coates | 606/99 |
| 5,180,384 A | * | 1/1993 | Mikhail | 606/80 |
| D337,639 S | * | 7/1993 | Beckman | D24/133 |
| 5,275,603 A | * | 1/1994 | Ferrante et al. | 606/86 |
| 5,308,350 A | | 5/1994 | Mikhail | |
| 5,554,158 A | * | 9/1996 | Vinciguerra et al. | 606/80 |
| 6,783,551 B1 | * | 8/2004 | Metzger et al. | 623/20.31 |
| 2005/0033444 A1 | * | 2/2005 | Jones et al. | 623/22.12 |

OTHER PUBLICATIONS

Brochure entitled: *Unicompartmental Knee System*, The Miller/Galante Advantage, Zimmer Inc. 1988, 1992.
Brochure entitled: *Patellar Femoral Systems*, AGC Total Knee System, Biomet, Inc., 1989.

* cited by examiner

*Primary Examiner*—Eduardo C. Robert
*Assistant Examiner*—James L Swiger
(74) *Attorney, Agent, or Firm*—Emch, Schaffer, Schaub & Porcello Co., L.P.A.

(57) ABSTRACT

A femoral impactor-extractor and method includes a body having an elongated passageway extending from a proximal end to a distal end, an elongated post positioned in such passageway for longitudinal movement therein and extending from a threaded proximal end to a distal end having an enlarged flange with a greater length than breadth. The proximal end of the elongated post is threaded and threadedly engaged to a rotatable handle. Rotation of the handle moves the elongated post and its flange in a proximal direction to clamp the femoral knee prosthesis between the ends of the flange and contoured surfaces which engage the articulating surfaces of the respective condylar portions of the prosthesis.

11 Claims, 6 Drawing Sheets

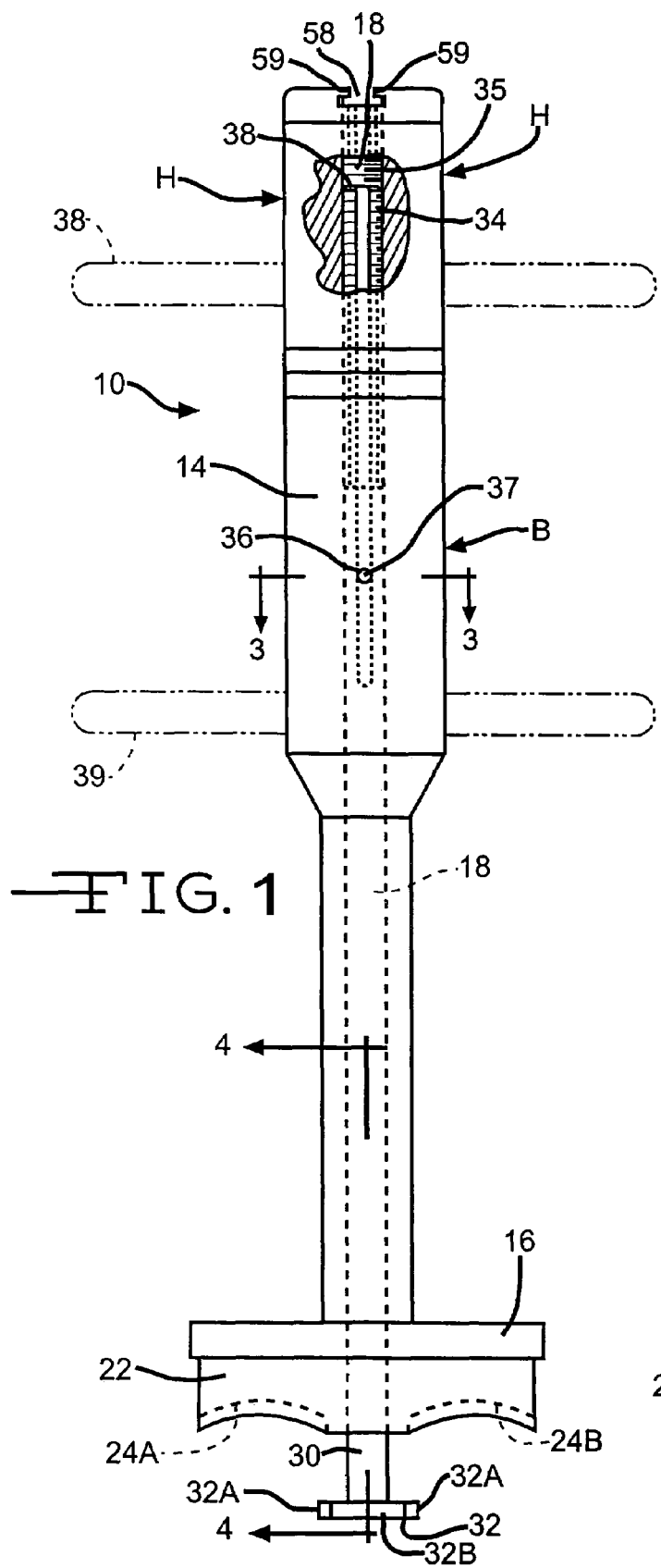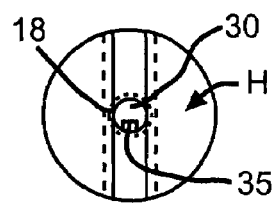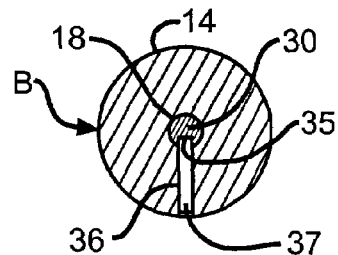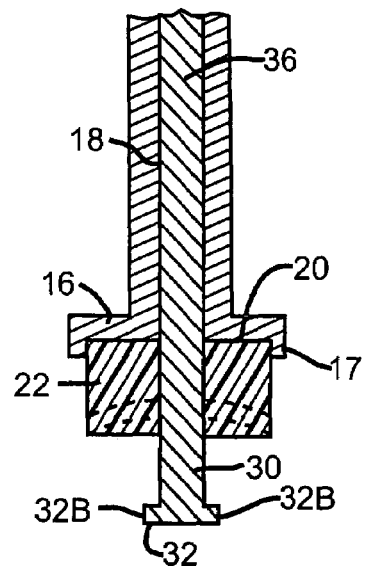

FEMORAL IMPACTOR-EXTRACTOR

BACKGROUND OF THE INVENTION

In performing knee replacement surgery, it is recognized that a femoral knee prosthesis implanted at the distal end of the prepared femur may require resection and replacement after a period of years. It is important that any removal of a previously implanted femoral prosthesis be done in a manner which causes minimal damage to the bone so that the bone can be readily resected to receive a new prosthesis.

The present invention permits the efficient removal of a previously implanted prosthesis with minimal damage to the bone at the distal end of the femur and also permits effective implantation of a knee prosthesis in initial and revision surgery.

SUMMARY OF THE INVENTION

The present invention is directed to an impactor-extractor which snuggly grips a femoral knee prosthesis for (a) extracting a previously implanted femoral prosthesis during revision surgery or (b) implanting a femoral prosthesis during initial or revision surgery. With the prosthesis firmly gripped by the impactor-extractor of the present invention, the surgeon can readily position the prosthesis in correct alignment during implantation, including where necessary, striking the impactor-extractor with a hammer to drive the gripped knee prosthesis to the correct position firmly into engagement with the prepared distal end of the femur. When used to extract a previously implanted prosthesis, the prosthesis may be similarly gripped and, where necessary, the impactor-extractor impacted outwardly to assist in removal. If desired, the prosthesis to be removed may have a recess or notch on its superior surface adjacent each side facing the intercondylar notch.

Accordingly, it is an object of the present invention to provide instrumentation which is useful in the implantation and removal of a femoral knee prosthesis.

It is a further object of the present invention to provide a method for implanting and/or extracting a femoral knee prosthesis.

It is an additional object of the present invention to provide a femoral impactor-extractor useable in combination with a prosthesis designed to facilitate its engagement thereby.

Other objects and advantages of the present invention will become apparent to those skilled in the art upon a review of the following detailed description of the preferred embodiments and the accompanying drawings.

BRIEF DESCRIPTION OF THE DRAWINGS

FIG. 1 is an elevational view, partly in section, of the impactor-extractor of the present invention.

FIG. 2 is a top view of the handle portion of the impactor-extractor.

FIG. 3 is a sectional view taken through line 3-3 of FIG. 1.

FIG. 4 is a sectional view taken through line 4-4 of FIG. 1.

DETAILED DESCRIPTION OF THE PREFERRED EMBODIMENTS

Figure 5:
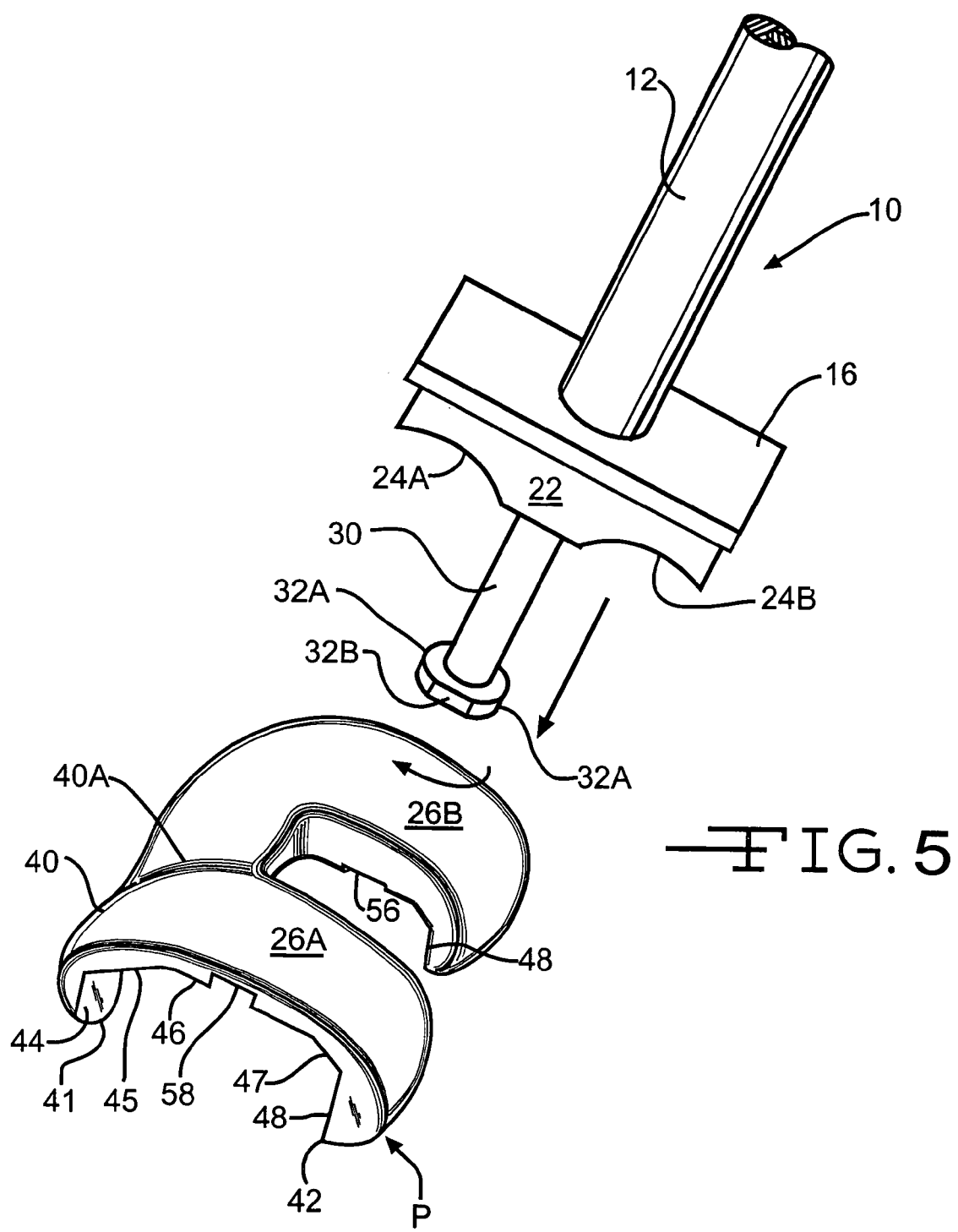
FIG. 5 is a perspective view showing the impactor-extractor about to be inserted in the intercondylar notch of a femoral knee prosthesis for gripping such prosthesis preparatory to implantation or extraction.

Referring to FIGS. 1-7, there is shown a first embodiment of impactor-extractor generally designated by the numeral 10. The impactor-extractor 10 includes a main body component B and a handle H rotatably moveable relative thereto. The body component B includes an elongated housing having a central cylindrical section 12, an enlarged gripping section 14 extending proximally from the central cylindrical section 12 and a support section 16 extending radially from the distal end of the central cylindrical section 12. A central passageway 18 extends throughout the body section B including through the support section 16, central cylindrical section 12 and enlarged gripping section 14. Preferably, the enlarged gripping section 14 has a roughened surface 15 to provide enhanced gripping ability. (See FIG. 6).

As can be seen in FIG. 4, the support section 16 includes a distally extending flange 17 which cooperates with the laterally extending portion of the support section 16 to define a distally facing pocket 20.

Figure 6:
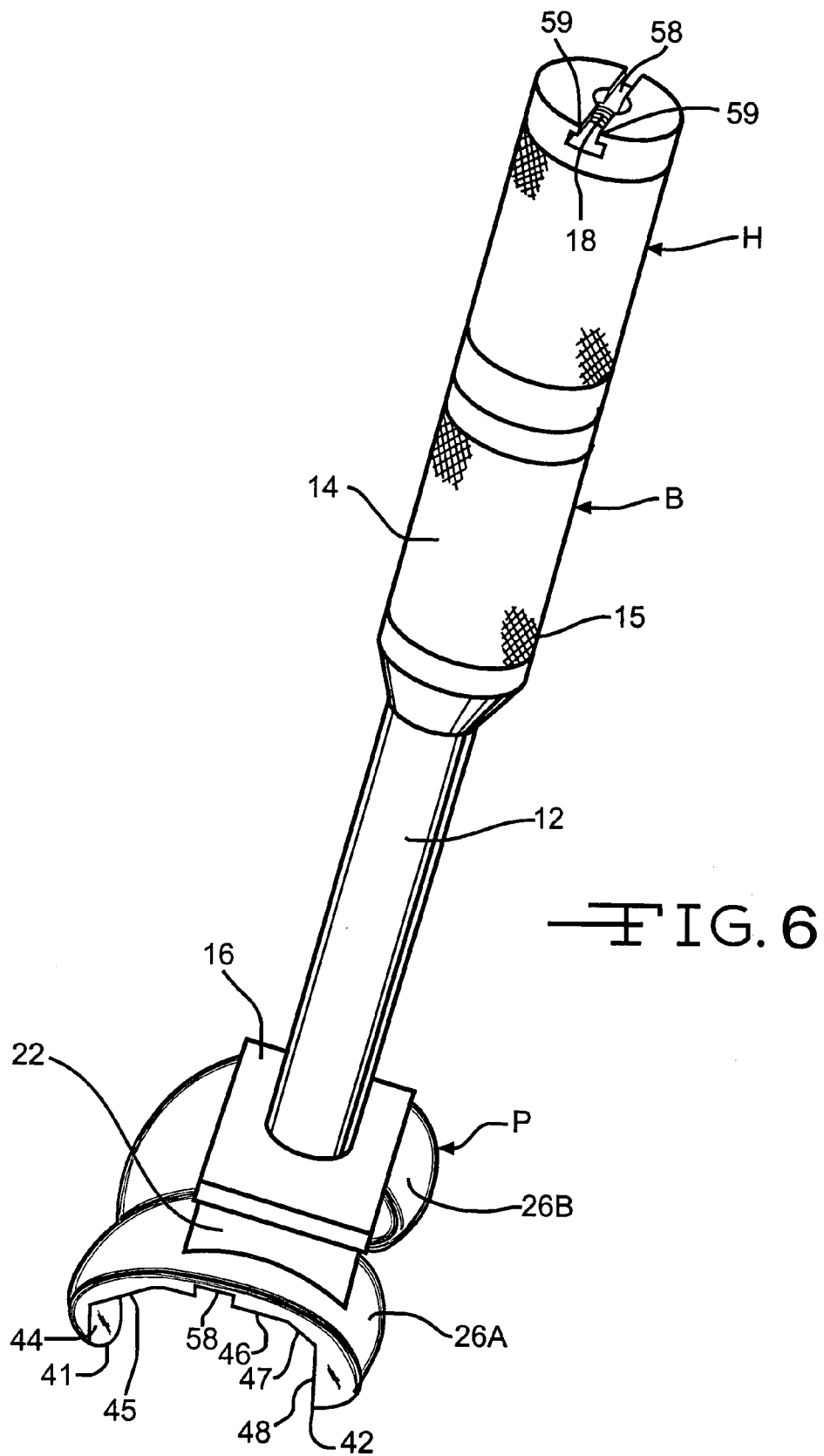
FIG. 6 is a perspective view showing the impactor-extractor firmly gripped to the femoral prosthesis.
Figure 7:
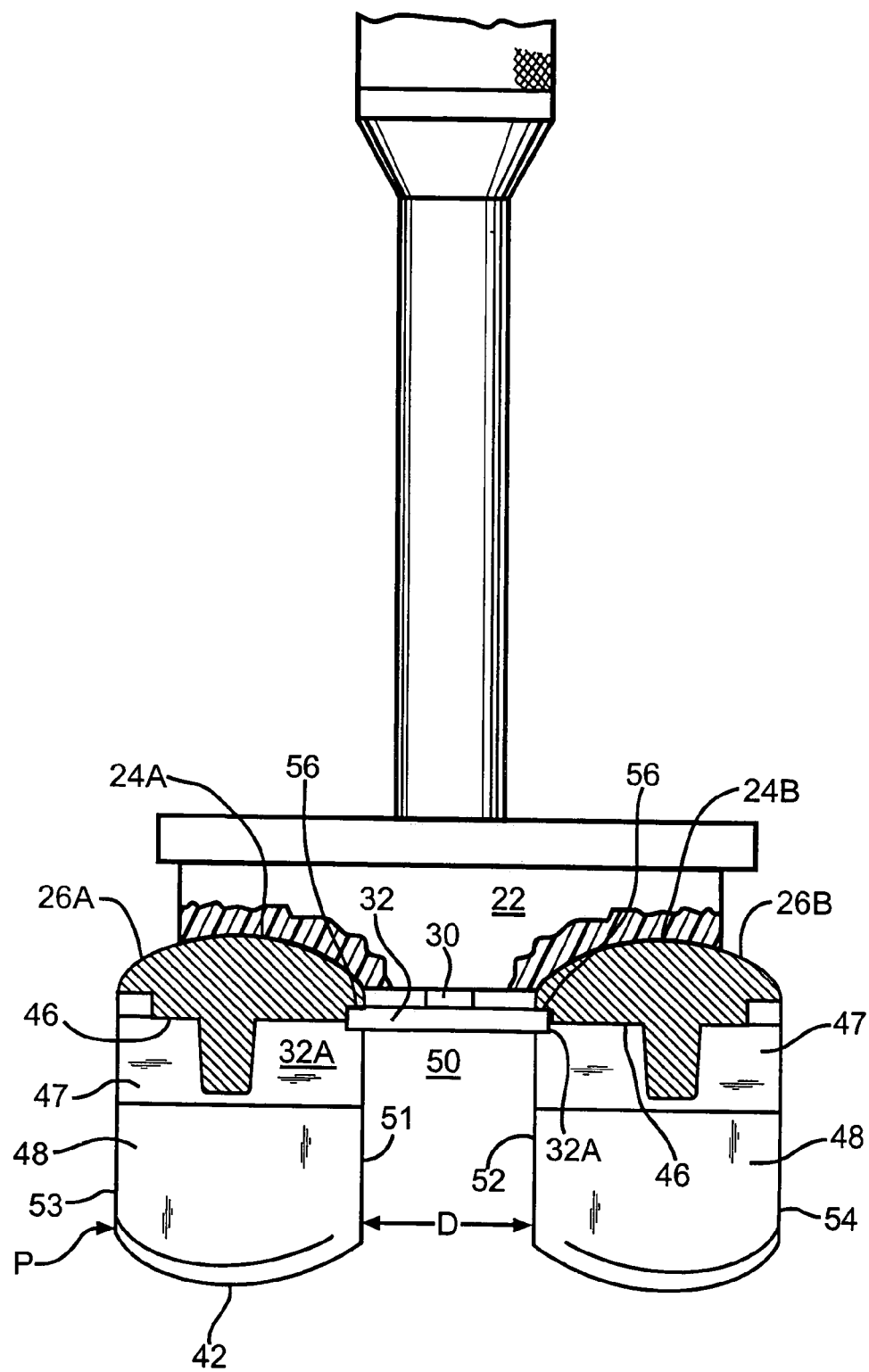
FIG. 7 is an elevational view, partially in section, showing the impactor-extractor gripped to the femoral knee prosthesis.
Figure 9:
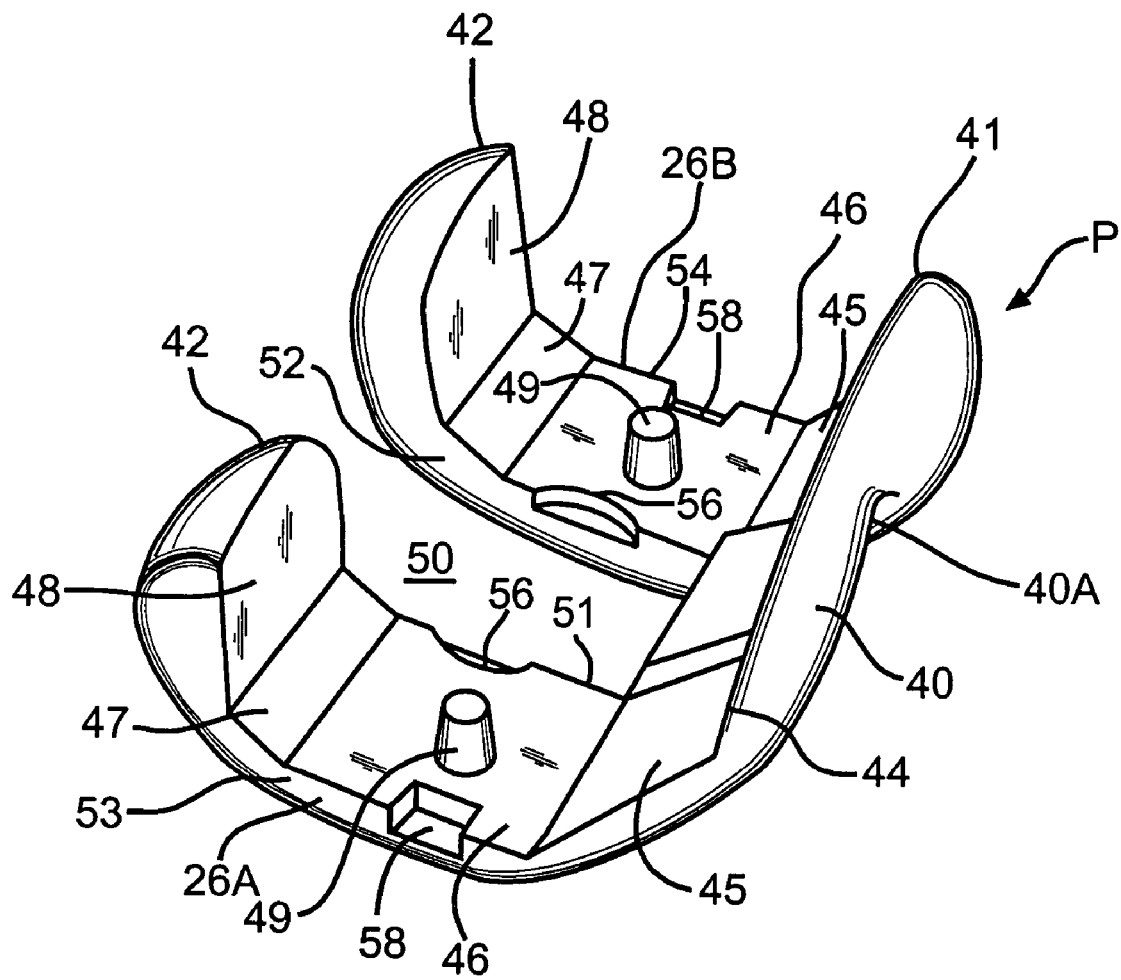
FIG. 9 is a perspective view of a modified femoral knee prosthesis having a notch which can be readily engaged by the impactor-extractor.

Positioned in the pocket 20 is a condylar engagement member 22, the distal surface of which has two contoured recesses 24A and 24B shaped to receive the articulating condylar surfaces 26A and 26B of a femoral knee prosthesis P (see FIGS. 6, 7 and 9).

Extending through the passageway 18 is an elongated post 30, the distal end of which extends radially outwardly from the axis of the post 30 to define a gripping flange 32. As can be seen most clearly in FIGS. 1, 4 and 5, the gripping flange 32 is oblong, having a major axis extending between ends 32A following an arcuate path and a minor axis extending between centers of opposing flats 32B. The length of the gripping flange 32 between ends 32A is longer than the width between the opposing flats 32B. Although it is preferred that the ends 32A follow an arcuate path, they could also follow a straight-line path.

The elongated post 30 extends to a proximal end 38 positioned in the handle H. That portion of the elongated post 30 adjacent the proximal end 38 is provided with outwardly facing threads 34 which are engaged to inwardly facing threads 35 in that portion of the central passageway 18 extending through the handle H. Rotation of the handle H relative to the enlongated post 30 will result in the post 30 moving in a proximal direction if the handle H is turned in one direction and in a distal direction if the handle H is rotated in the opposite direction. Movement of the post 30 in the proximal direction will move the gripping flange 32 closer to the support section 16 and its condylar engagement member 22 preparatory to gripping the prosthesis P.

In order to rotate the handle H relative to the elongated post 30, there is provided means for preventing rotational movement of the post 30 relative to the main body B. This is accomplished by providing a longitudinally extending groove 35 facing outwardly of the elongated post 30. The body portion B is provided with a lateral passageway 36 extending inwardly from the enlarged gripping section 14 outer periphery to the central passageway 18, preferably at substantially right angles thereto. A pin 37 is snugly received in the lateral passageway 36 and extends into the groove 35. The positioning of the pin 36 in the body B with its end extending into the groove 35 functions to prevent rotational movement of the elongated post 30 relative to the body B while permitting longitudinal movement therein when the handle H is rotated. As previously noted, rotation of the handle H relative to the body B will cause the elongated post 30 and the gripping flange 32 at the distal end thereof to move proximally or distally in the passageway 18 depending on the direction of rotation. Upon such proximal or distal movement of the elongated post 30, the longitudinal groove 35 will move axially relative to the pin 37 but will not rotate relative to the body B.

If desired, laterally extending handles 38 (shown in phantom in FIG. 1) may be provided for the handle H and laterally extending handles 39 (shown in phantom in FIG. 1) may be provided for the enlarged gripping section 14 in order to assist in providing a good grip.

The proximal end of the handle H is provided with a groove 58 extending at a right angle to the axis of the central passageway 18. The groove 58 is undercut on opposite side to provide spaced apart flanges 59. The groove 58 can receive a tool to assist in removal of a prosthesis. Retention of the tool may be assisted by the tool sliding in the opposed undercut areas for engagement by the flanges.

The impactor-extractor 10 is sized to readily function with a prosthesis P of a type typically used in total knee arthroplasty. An example of one such type of femoral knee prosthesis is one manufactured by Zimmer Inc. as its Insall/Burstein II modular knee system or its Model 1332-02,03 Geometric Femoral Prosthesis. Another type of prosthesis is shown in U.S. Pat. No. 6,123,729.

Although the impactor-extractor 10 can be used with prior art femoral prostheses, it is preferable to provide a modified femoral prosthesis incorporating recesses in the superior bone engaging surfaces of opposing condylar portions to receive the gripping flange 32, specifically, the ends 32A lying on the major axis.

As shown in FIGS. 5-9, the prosthesis P is a one-piece unitary construction and includes a patellar flange area 40 extending from a first or anterior end 41, a first condylar portion 26A and a second condylar portion 26B, each of which extend from the patellar flange area 40 to a second or posterior end 42. As will be appreciated by those skilled in the art, the prosthesis P could be used for implantation in either a right knee or left knee and the first and second condylar portions 26A, 26B will be either lateral or medial depending upon the knee in which the prosthesis P is implanted. Other types of knee prostheses with which the impactor-extractor 10 could be used are ones designed specifically for the right knee or left knee.

The patella flange area 40 has a patella engaging surface 40A shaped to allow anatomical tracking of a natural or prosthesis patella and defining a portion of an inferior articulating surface of the prosthesis P. The patella engaging surface 40A blends smoothly with the articulating surface defined by the first and second condylar portions 26A, 26B.

As shown in FIGS. 5-9, the knee prosthesis P has a superior bone engaging surface with a series of bone engaging flats 44, 45, 46, 47 and 48. As can be clearly seen in FIG. 5, there are two sets of such flats 46, 47 and 48 in the areas underlying the condylar portions, namely, one set in the area underlying the first condylar portion 26A and the second set in the area underlying the second condylar portion 26B. Each of the flats 46 has a fixation post 49 extending therefrom. There are single flats 44 and 45 in the area between the condylar portions 26A, 26B and anterior end 41.

The condylar portions 26A and 26B of the prosthesis P are separated from one another by an intercondylar notch 50 which is defined by a first inner wall section 51 extending superiorly from the articulating surface of the first condyle 26A and a second inner wall 52 extending superiorly from the articulating surface of the second condylar portion 26B. Preferably, the inner walls 51 and 52 are parallel to one another and are spaced apart from one another by a distance D as shown in FIG. 7. The first condylar portion 26A also has an outer wall 53 extending superiorly from its articulating surface 26 and the second condylar portion 26B has a second outer wall 54 extending superiorly from its articulating surface.

Each of the condylar portions 26A, 26B is provided with a notch 56 which extends outwardly from the first inner wall 51 in the case of condylar portion 26A and upwardly from its flat 46 toward its articulating surface and outwardly from the inner wall 52 of condylar portion 26B and upwardly from its flat 46 toward its articulating surface. The depth of the notch 56 upwardly from the flat 46 toward the articulating surface of the respective condyles 26A, 26B is at least equal to the thickness of the gripping flange 32. The breadth of the respective notches 56 is sufficiently great to receive the gripping flange 32 in an area adjacent the ends 32A. The breadth of the gripping flange 32 from one side 32B to the opposing side 32B is smaller than the size of the gap D between the inner walls 51 and 52; however, the length of the gripping flange 32 from the end 32A to the opposing end 32A along the longitudinal axis is greater than the distance D representing the spacing between the respective inner walls 51 and 52. Accordingly, it is possible to insert the elongated post 30 and its gripping flange 32 into the space defined by the intercondylar notch 50 without interference from the inner walls 51 and 52 provided that the post 30 and its flange 32 are in a position in which the longitudinal axis defined by a line extending between the outermost portions of the ends 32A is parallel to the walls 51 and 52. Following positioning of the flange 32 in the gap 50 and at a distal position aligned with the respective notches 56, the impactor-extractor 10 may be manipulated by the surgeon rotating the body portion B and the elongated post 30 and gripping flange 32 carried thereby 90° more or less in order to position those portions of the flange 32 at ends 32A in the notches 56 for engagement therewith.

If desired, the femoral knee prosthesis P may also have a notch 58 formed at the junctures of the outer walls 53, 54 with their respective flats 46.

Figure 8:
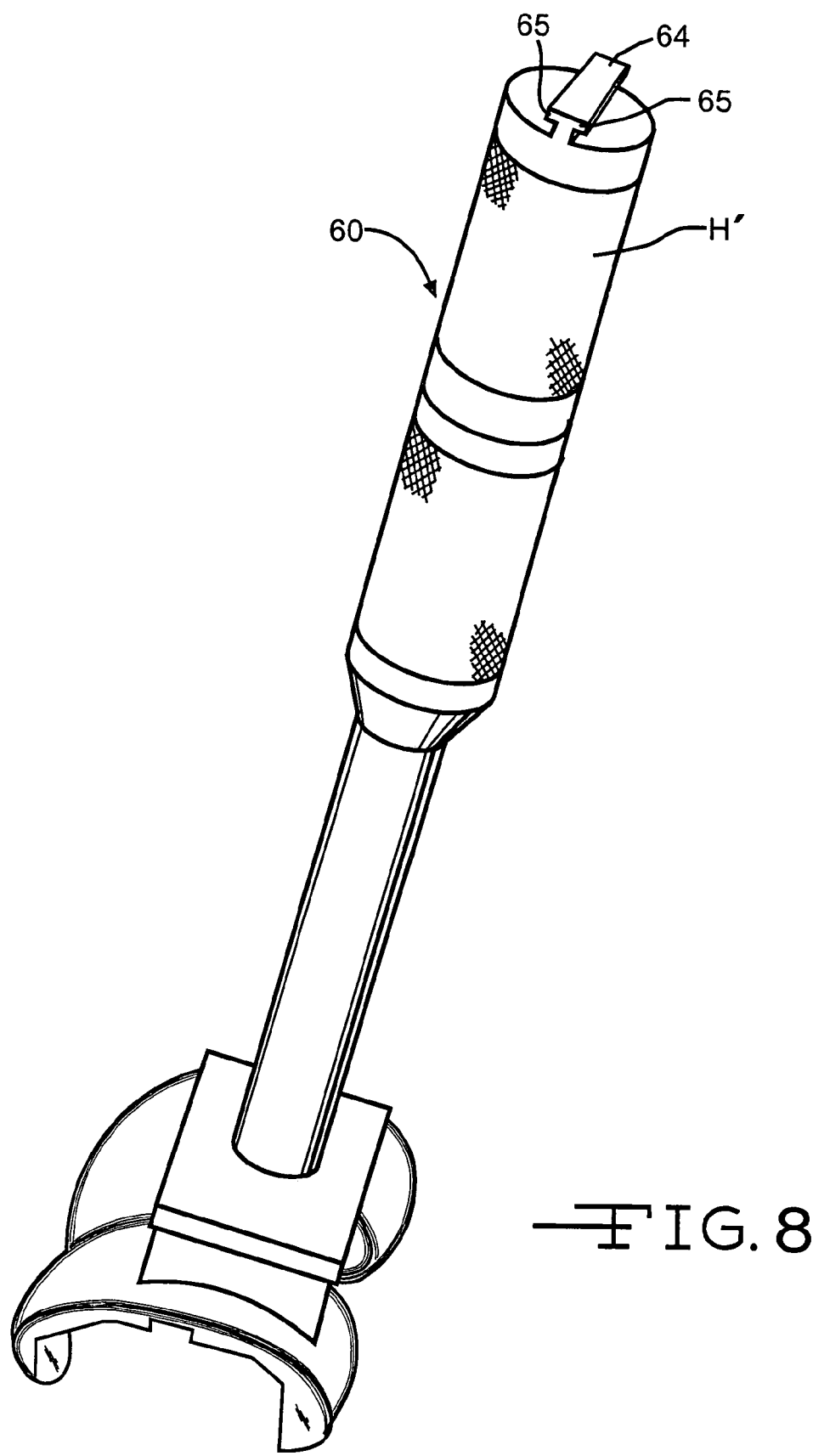
FIG. 8 is a perspective view of a modified embodiment.

FIG. 8 shows a modified impactor-extractor 60. The impactor-extractor 60 is identical to the impactor-extractor 10 of the previous embodiment with the exception that it has a handle H in which the proximal end is provided with a diagonally extending extension 64 with a pair of outwardly extending flanges 65 defining undercut slots for receiving a tool.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. Apparatus for positioning or removing a femoral knee prosthesis having first and second condylar portions, each said condylar portion having an articulating surface extending proximally to distally, a superior surface for engagement with a prepared surface at the distal end of a femur, each of said condylar portions having an inner edge between its said articulating surface and superior surface, said inner edges defining a gap, said apparatus comprising
   (a) an elongated housing extending from a distal end to a proximal end;
   (b) a passageway extending through said housing along an axial path;
   (c) a condylar engagement member at the distal end of said housing, said member having a first condylar engagement surface and a second condylar engagement surface spaced from said first condylar engagement surface, said condylar engagement member having an aperture between said first and second condylar engagement surfaces; and
   (d) a post having a longitudinal axis positioned in said passageway for axial movement therein and extending through said condylar engagement member, said post having an outwardly extending flange at its distal end, said flange having first and second edges spaced apart to define a breadth smaller than said gap and first and second ends spaced apart to define a length greater than said gap, said post and flange being rotatable together about said longitudinal axis from a first position in which said breadth is aligned to permit movement of said flange through said gap to a second position in which said length spans said gap to align said first and second ends with said superior surface on opposite sides of said gap, said post being movable axially to a position at which said flange first and second ends, upon rotation to said second position, engage said superior surface while said condylar engagement member is engaged to said first and second condylar portions.

2. Apparatus of claim 1 wherein said post has threads spaced from said flange and further including a rotatable handle threadedly engaged to said threads, rotation of said handle moving said flange toward or away from said condylar engagement member.

3. Apparatus of claim 2 further including means to prevent rotation of said post in said housing.

4. Apparatus of claim 2 further including a longitudinally extending slot in said-post and an abutment extending from a fixed position on said housing and into said slot to prevent rotation of said post in said housing while permitting axial movement of said post in said passageway.

5. Apparatus of claim 2 wherein said handle has a proximal end spaced from said housing, said proximal end having a diagonally extending slot for receiving a tool, said slot being undercut to define at least one tool retention surface.

6. Apparatus of claim 2 wherein said handle has a proximal end spaced from said housing, said proximal end having a diagonally extending abutment at said proximal end for receiving a tool, said abutment including at least one flange spaced from said proximal end for retaining said tool.

7. A method for positioning or removing a femoral knee prosthesis having first and second condylar portions, each said condylar portion having an articulating surface extending proximally to distally, a superior surface for engagement with a prepared surface at the distal end of a femur, each of said condylar portions having an inner edge between its said articulating surface and superior surface, said inner edges defining a gap, comprising the steps of
   (a) providing an instrument for gripping said knee prosthesis, said instrument having:
      (i) an elongated housing extending from a distal end to a proximal end;
      (ii) a passageway extending through said housing along an axial path;
      (iii) a condylar engagement member at the distal end of said housing, said member having a first condylar engagement surface and a second condylar engagement surface spaced from said first condylar engagement surface, said condylar engagement member having an aperture between said first and second condylar engagement surfaces; and
      (iv) a post positioned in said passageway for axial movement therein and extending through said condylar engagement member, said post having an outwardly extending flange at its distal end, said flange having a first and second edges defining a breadth smaller than said gap and first and second ends defining a length greater than said gap;
   (b) moving said flange through said gap;
   (c) rotating said instrument including said post to a position such that said flange spans said gap;
   (d) engaging said first condylar engagement surface to said first condylar portion articulating surface and said second condylar engagement surface to said second condylar portion articulating surface; and
   (e) moving said post axially to thereby engage said flange to said superior surface on opposite sides of said gap.

8. The method of claim 7 wherein said instrument includes a rotatable handle threadedly engaged to said post and further including the step of rotating said handle to move said flange toward said condylar engagement surfaces.

9. The method of claim 8 further including the step of restraining said post from rotation while rotating said handle.

10. The method of claim 8 further including the step of providing at least one engagement abutment on said handle and engaging an instrument to said abutment.

11. The method of claim 7 further including the steps of providing a first recess at the juncture one of said inner edges and said superior surface, a second recess at the juncture of the other of said inner edges and said superior surface and positioning said flange first end in said first recess and said flange second end in said second recess following the step of moving said flange through said gap.

* * * * *